US008954166B2

(12) United States Patent
Pettinelli

(10) Patent No.: US 8,954,166 B2
(45) Date of Patent: Feb. 10, 2015

(54) INDUCED MODULATION OF NEURONAL TRANSMISSION

(76) Inventor: Eugene Eustis Pettinelli, Sudbury, MA (US)

(*) Notice: Subject to any disclaimer, the term of this patent is extended or adjusted under 35 U.S.C. 154(b) by 963 days.

(21) Appl. No.: 12/488,578

(22) Filed: Jun. 21, 2009

(65) Prior Publication Data

US 2010/0324642 A1  Dec. 23, 2010

(51) Int. Cl.
*A61N 1/36* (2006.01)
*A61N 1/05* (2006.01)

(52) U.S. Cl.
CPC ............ *A61N 1/0556* (2013.01); *A61N 1/3605* (2013.01); *A61N 1/36067* (2013.01)
USPC ........................................... 607/118

(58) Field of Classification Search
CPC ......... A61N 2/00; A61N 2/002; A61N 2/004; A61N 2/006; A61N 2/02; A61N 1/0551; A61N 1/0556; A61N 1/06; A61N 1/3605
USPC .............................. 607/118; 600/554
See application file for complete search history.

(56) References Cited

U.S. PATENT DOCUMENTS

| 3,841,306 | A  | * | 10/1974 | Hallgren | 600/13 |
|---|---|---|---|---|---|
| 4,573,481 | A  | * | 3/1986 | Bullara | 607/118 |
| 2007/0106339 | A1 | * | 5/2007 | Errico et al. | 607/42 |
| 2007/0142870 | A1 | * | 6/2007 | Knudson et al. | 607/40 |
| 2008/0183237 | A1 | * | 7/2008 | Errico et al. | 607/40 |

\* cited by examiner

*Primary Examiner* — Eric D. Bertram

(57) ABSTRACT

The invention is directed to a method of treating movement disorders by the modulation of neuronal transmission using time-variant non-conservative magnetic fields. The invention is also directed to a method for treating dystonias.

20 Claims, 2 Drawing Sheets

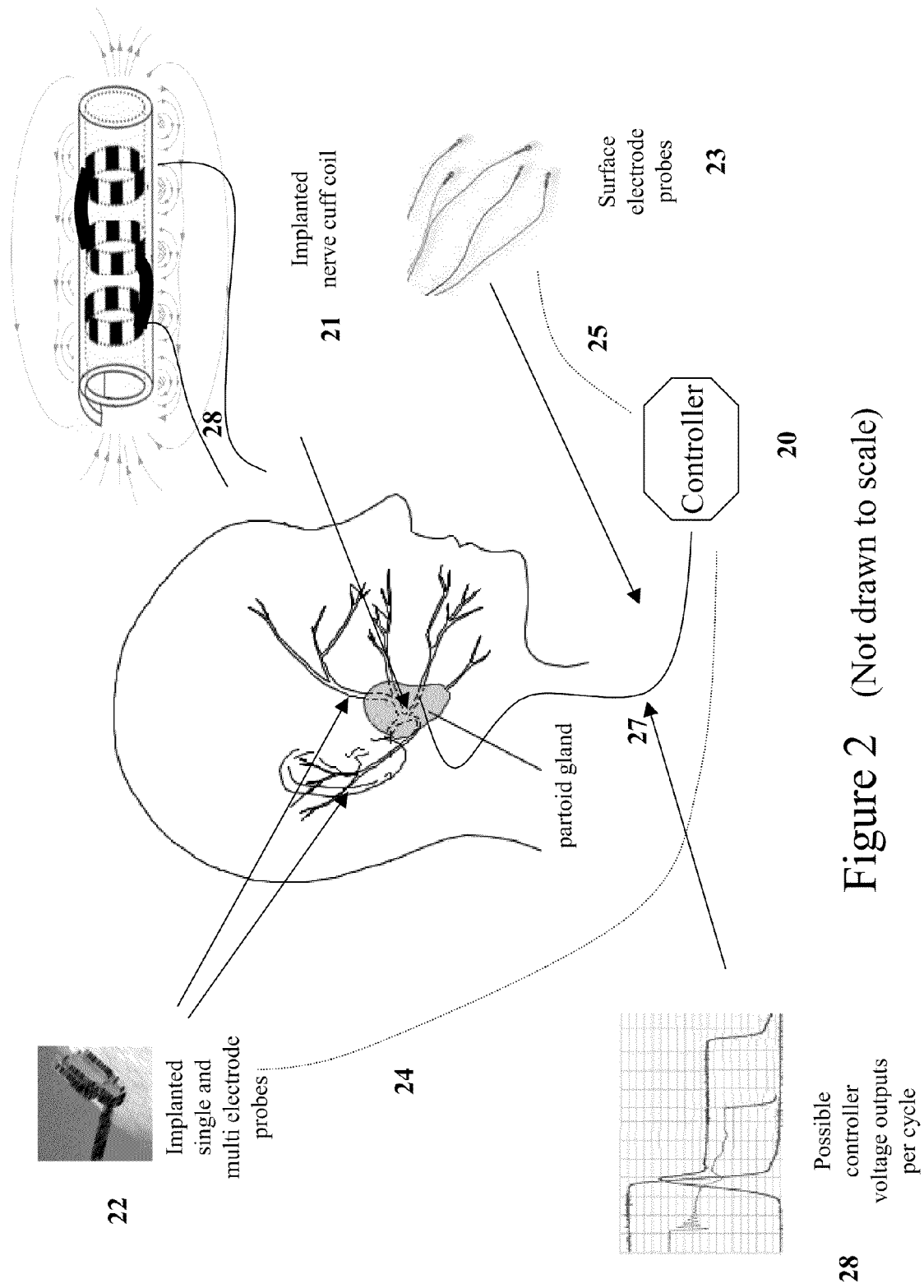
Figure 2 (Not drawn to scale)

INDUCED MODULATION OF NEURONAL TRANSMISSION

FIELD

Embodiments of the present applicant relate to the field of neurophysiology. More specifically, exemplary embodiments relate to inducing non-linear changes in signal propagation in the peripheral and central nervous systems.

BACKGROUND

Proper functioning of motor nerves is critical to survival and even minor impairments can have a negative impact on the socioeconomic capacity of an individual's life. Even non-life threatening conditions such as hemifacial spasm and other focal dystonias can progress to a point where the quality of life is severely impaired.

Many types of nerves are very complex, for example the facial nerve is formed from the motor neurons that innervate the facial muscles and from the nervous intermedius of Wrisberg which contains preganglionic parasympathetic fibers. As such it is a mixed nerve with special visceral efferent, general visceral efferent, special visceral afferent, and general somatic afferent functions.

Improper functioning of nerves such as this can result from many causes including infection, tumor growth, and trauma. The pathophysiological mechanisms underling hemifacial spasm, for example, include the ectopic generation of discharges which can reach up to 150 impulses per second with irregular burst repetitions, ephaptic transmission and the lateral spread of excitation between facial axons. After continuous antidromic bombardment of inputs, a hyperexcitability of facial motoneurons can occur, the initial cause in most cases being a zone of demyelination at the root exit zone of the facial nerve.

Treatment and rehabilitation of many nerve diseases can be very difficult depending on the type and stage of development. In many cases, however, the etiology is not known, such as in benign essential blepharospasm, meige disease, and other related dystonias. For hemifacial spasm, treatment includes Botulinum toxin injections, facial nerve denervation, and surgical decompression of the offending vessel or vessels.

Disruption of aberrant neuronal activity patterns through stimulation is a useful approach to treating movement disorders, for example, electrical deep-brain stimulation has been found to be a helpful complement to dopamine replacement therapy for treating motor symptoms in Parkinson's disease. The low-frequency synchronous cortiostriatal oscillations can be controlled, but at the cost of a highly invasive surgical procedure which implants electrodes in such areas as the basal ganglia. Here the metal electrodes create an electrical field that affects the nearby cells. In order for the electrical pulses to activate the neuronal elements, it must drive ions across the cell membrane, and the lines of electrical force from the cathode to the anode must therefore be perpendicular to the membrane. Mutipolar electrodes are used to shape the electric field to more closely conform to the complexity of the tissue being treated and allows for more flexibility in spread and intensity. A useful overview of this can be found in "Deep Brain Stimulation Programming" by Montgomery, Feb. 20, 2006.

A more recent approach looks at implanting light-activated chloride pumps into the primary excitatory neuron in the subthalamic nucleus. (see page 1555, Science, Vol 323 Mar. 20, 2009). Stimulating peripheral nerves to affect oscillatory neuronal activity in the brain would be a less invasive approach, and is of considerable current interest.

Transcranial magnetic stimulation has also been used over the years to affect the behavior of nervous tissue and has been applied to peripheral nerves with some efficacy. It operates on the principal of induction which produces a magnetic field oriented orthogonally to the plane of the coil. The current induced in the structures of the brain activates nearby nerve cells in unpredictable ways, even with the advent of new coil types such as the Hesed Coil which allows for deeper penetration without inducing a much greater stimulation of superficial cortical regions.

While the above techniques are useful in stimulating neuronal tissue, in many cases of disease, and especially in dystonias, what is desired is the quieting, not the additional stimulation, of harmful signals which cause uncontrolled motor responses. Because these harmful signals typically form a stochastic process, and are embedded within a stream of otherwise healthful signals, then what is desired is a method to control them without harming the nerve, its components, or the surrounding tissue. Also, because in may of the dystonias the exant cause of continuation of spasm is a harmful feedback loop, the need for continuous control is lessened, as intervening in a selected few time intervals can be sufficient to uncouple the feedback from the source.

SUMMARY OF THE INVENTION

An exemplary embodiment of the invention uses a sequence of time variant currents to induce a magnetic field within a cuff electrode coil surrounding a peripheral nerve. Because of the physics of the changing magnetic field which results from the time-variant currents, a non-conservative field is induced in the nerve. The nature of the induced electro magnetic field depends on the magnetic flux change through its surface, and by Faraday's law, the electric potential difference between any two points in the nerve depends on the path taken to measure it. This means, non-intuitively, that the voltage waveforms within the nerve can simultaneously be positive in one area and negative in another, at least over the course of time in which the magnetic flux is changing. A straightforward explanation of the physics for this can be found in MIT lecture notes Physics 8.02 Spring 2002, Apr. 1, 2002 and Mar. 15, 2002 by Profs. Walter Lewin and John Belcher.

This is important in controlling nerve signals because of their inherent complexity. Nerves such as the facial nerve can contain thousands of individual neurons, many of which are sensory and are sending signals in the opposite direction from the motor neurons. What is desired is the ability to control the behavior of both of these types of neuronal function simultaneously, so that, for example, the electrical wave that arises from the action potential is affected in each direction of propagation. The Schwann cells, in the case of the peripheral system, are critical to the effective transmission of the signals, are wrapped in a coiled configuration and as a result, the voltage path around them can be controlled. Placing the coiled electrode at the sites of the nodes of Ranvier, may be particularly effective in non-harmfully blocking a set offending signals. Similarly, the oligodendrocytes in the central nervous system have a parallel construction and can be influenced in a similar manner.

Means of constructing electrodes which can be implanted and surround nerves are well know, for example see Sawan et al: in the Turkish Journal of Electrical Engineering Vol 16, No 3, 2008, "Biomedical Circuits and Systems Dedicated for Sensing and Neurostimulation: Case study on Urinary Bladder Dysfunctions". Although in this instance their design is a split-cylinder cuff electrode with shape memory alloy armature embedded inside the cuff wall and functions as a simple anode/cathode combination, practitioners skilled in the art can envision the electrodes constructed in a coiled configuration. When the cuff is then snapped shut around the nerve, a connection is established with the other end of each loop of the coil. The coil and or coils can then be used for both sensing as well as for the creating of the time variant magnetic and electric fields. Construction of the cuff can be facilitated by low temperatures and the cuff structure revert to cylindrical shape around the nerve when exposed to body temperature. Where many loops of coil are needed to provide the necessary magnetic field strength, nanowires can be used because electropolymerization has become a convenient approach for producing conducting polymer materials from their corresponding redox-active monomers (see Nanotechnology 18 (2007) 424021 (7pp): "Individually Addressable Crystalline Conducting Polymer Nanowires in a Microelectrode Sensor Array" by Wang, et al.)

The methods of identification of offending signals in dystonias are well known in the art. For example, in hemifacial spasm aberrant motor induction signals can be detected readily by monitoring the lateral spread response of the facial nerve. Because the disease commonly arises from the ephaptic transmission of the facial nerve fibers caused by injury to the myelin, electromyography monitoring can easily detect by autocorrelation, the onset of a hyperexcited state of the motor neuron. The cuff electrode described above can be used either by itself to detect these signals, or it can be augmented by cuffs placed either along the same nerve or in other locations.

Sensing and control of the cuff coil is within the current scope of practice and can be accomplished by the use of an implantable sensor/stimulator such as described in the above article by Sawan et al., with the modification that the circuitry powers a coil rather than producing an electric charge for the creation of an action potential. As in the description by Sawan, the unit can be powered and/or controlled by an external device which interfaces with the implantable device via induction.

The particular shape, timing, and power of the waveform which drives the cuff coil is dependent on many variables including the nature and location of the particular disease state. An exemplary embodiment for hemifacial spasm would have a waveform with a rapid rise to induce a sufficiently large flux change in the cuff coil, leveling of the applied voltage for a time sufficient for the induced changes in the neuronal fiber to have the desired effect of blocking the various ionic flows, and an exponential decay reversing the previous effects so that the nerve can resume its normal and proper functioning. Control of the signal is a result of feedback derived from monitoring the lateral spread response from the coil or from a secondary sensor, which can be another cuff coil or a simple implanted electrode at the same or other location.

After the particular timings result in the diminution or extinction of the undesired emphatic transmissions, an advanced controller can create a baysian simulation of the otherwise stochastic signal, and apply the signal protocol in advance of the advent of the spasm's kindling response. Knowing when to stop the control signal is as important as knowing when to start it, and storing the parameters of the Bayesian model for shutoff timing would be a useful adjunct to the controller's functionality. A remote re-programming capability would also be useful in that alternative algorithms other than Bayesian can be installed and existing parameters can be to updated the controller's functionality.

BRIEF DESCRIPTIONS OF THE DRAWINGS

FIG. 2 is an illustration of elements of the invention as applied to hemifacial spasm, an exemplary embodiment.

DETAILED DESCRIPTION

Figure 1:
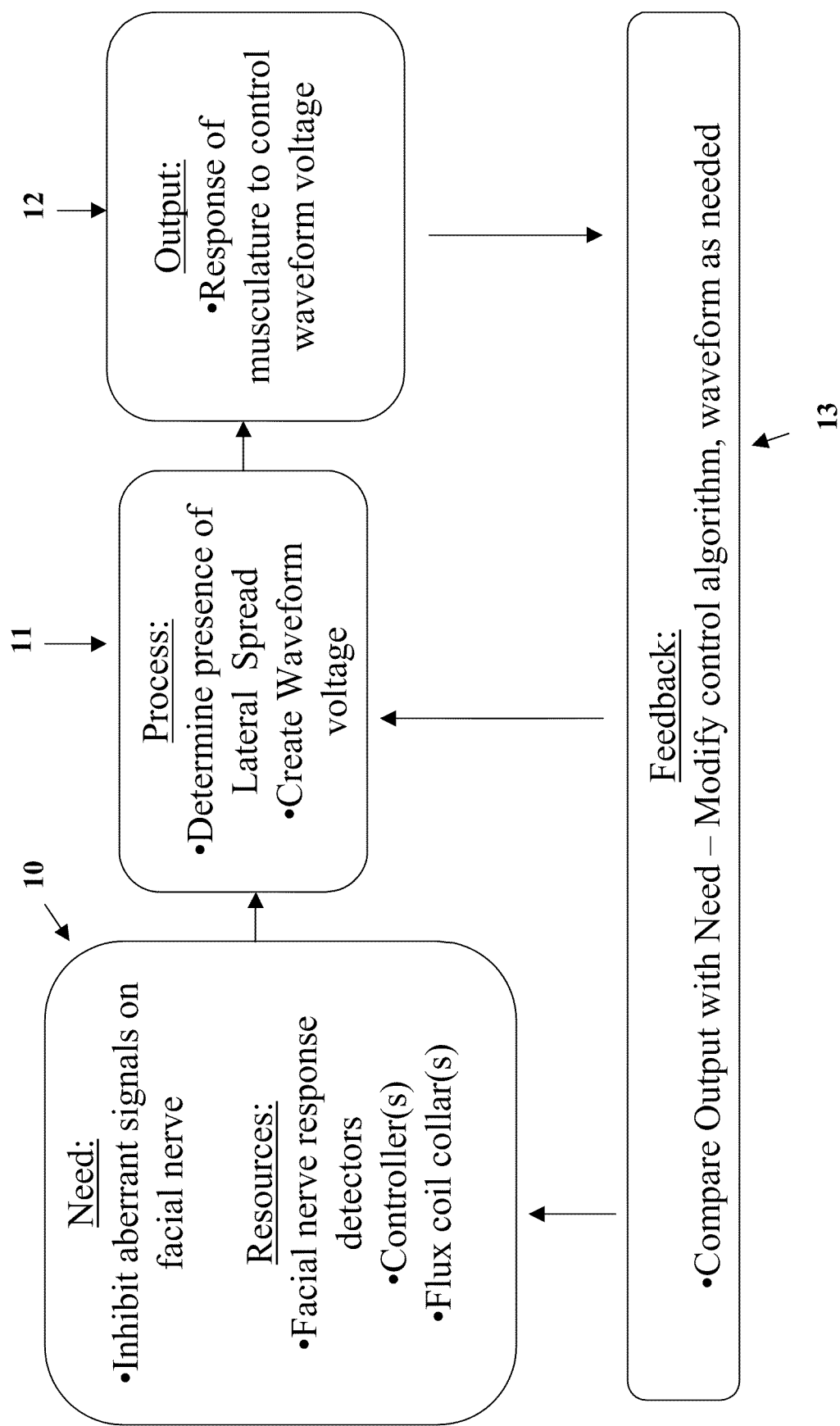
FIG. 1 is a diagram depicting universal system model of the high level functional flow for the control of hemifacial spasm, an exemplary embodiment.

An exemplary embodiment is described below with reference to the accompanying drawings. It should be understood that the following description is intended to describe the exemplary embodiment, and not to limit the invention defined in the appended claims.

FIG. 1 depicts a universal system model of the high level functional flow for the control of hemifacial spasm, an exemplary embodiment. The desired need 10 is to inhibit aberrant signals reaching the muscles from the facial nerve; the resources available are the sensors resident in the implanted or surface electrodes, the control collar which induces the magnetic fields and the controller which takes in the sensory data, and determines the proper response 11 based on current data, prior data and its outcome, and logic which determines the presence or absence of the lateral spread response and produces a voltage waveform which is expressed as a change in magnetic flux density by the coil collar which inhibits the facial nerve transmission for a specific time period and results 12 in the control of the target musculature. Results of the intervention are fed back 13 to the controller which changes the timeframe in which the voltage waveform is applied for maximal benefit. For example, if no lateral spread is detected then no control output is created, but if a single millisecond control voltage waveform inhibits the spread response, then the controller will wait until it appears again.

FIG. 2 is an illustration of elements of the invention as applied to hemifacial spasm, an exemplary embodiment; it is not drawn to scale. The implanted nerve control coil 21 consists of windings which when energized by a voltage from controller 20 produces a flux in proportion to amplitude and time derivative of the voltage wave. The control coil can consist of one or multiple coils located at optimal locations, for example on a node or nodes of Ranvier which act like switching stations to re-establish the action potential lost in transmission to that point. Controller 20 can be located in any convenient location, including externally, but is best positioned in the chest similarly to implantable caridoverter defibrillators, and even if internal it can be controlled, re-programmed, and re-charged externally.

The sensors 22 of the nerve action potentials and muscle response can be single or muti-electrode connected to the controller via control wires 24. Sensory elements can include surface electrode probes 23 which are connected by wires or wirelessly to controller 20. Control cuff 21 can also be used as a sensor of either electric or magnetic fields, and can be connected by wires 28 to the controller 20.

Depending on the nature and timing of the inputs derived from the sensors, for example the detection of a lateral spread response, from sensors 22, 23 and sometimes 21, the controller 20 produces voltage outputs 28 that are timed to intervene with the abnormal flow of action potential in the nerve. There types of possible controller voltage output waveforms 28 is large and situation dependent, but is most likely to be initially characterized by a sharp initial increase (or sharp initial reverse current flow to create the opposite flux density in the cuff coil) followed by a sharp decrease, or other casts by a more gradual decline. The timing of the outputs 28 can vary, but are likely to initially in the millisecond range. The number of pulse outputs will vary greatly depending on the type of intervention needed, and can be as few as one per detected abnormality.

The results of the controller 25 voltage output waves are determined by the construction of the particular nerve cuff coil, which will change depending on the particular person, condition, and type of nerve being affected. Because of Faraday's law, as discussed above, the electric potential difference between any two points in the nerve depends on the path taken to measure it. This means, non-intuitively, that the voltage waveforms within the nerve that are created by the flux change of the cuff coil 21 can simultaneously be positive in one area and negative in another, at least over the course of time in which the magnetic flux is changing. Thus the ionic flow of the sensory and motor neurons within the nerve, of which there can be thousands, can, on a time-transient basis, be controlled at the same time even though they require the simultaneous imposition of voltages that could not be sustained in static environment.

REFERENCES CITED

1. "Deep Brain Stimulation Programming" by Montgomery, Feb. 20, 2006. https://mywebspace.wisc.edu/ebmontgomery/web/
2. "Neuropsychiatry: Rewiring Faulty Circuits in the Brain", Greg Miller, page 1555, Science, Vol 323 Mar. 20, 2009.
3. Lecture, Physics 8.02 Spring 2002 , Apr. 1, 2002 and Mar. 15, 2002 by Profs. Walter Lewin and John Belcher.
4. "Biomedical Circuits and Systems Dedicated for Sensing and Neurostimulation: Case study on Urinary Bladder Dysfunctions". Sawan et al: in the Turkish Journal of Electrical Engineering Vol 16, No 3, 2008.
5. Individually Addressable Crystalline Conducting Polymer Nanowires in a Microelectrode Sensor Array" by Wang, et al. Nanotechnology 18 (2007)

What is claimed is:

1. A method of controlling a nerve with one or more magnetic fields, the method comprising:
    surrounding at least one nerve with at least one coiled collar,
    placing at least one sensor for the at least one nerve such placing being at a location along the same nerve,
    connecting the at least one sensor and the at least one coiled collar to a controller,
    obtaining nerve activity information from the at least one sensor,
    based on the nerve activity information, calculating a voltage waveform to disrupt creation of action potentials by the nerve,
    inducing a magnetic field by administering the calculated voltage waveform to the coiled collar.
2. The method of claim 1, wherein the voltage waveform consists of one of voltage and voltage regulated current.
3. The method of claim 1, wherein the coiled collar performs the non-simultaneous roles of sensor and administering the calculated waveform.
4. The method of claim 1 wherein the placing of the at least one sensor comprises the placing of at least one of implanted and surface electrode.
5. The method of claim 1 wherein the placing of the at least one sensor comprises the placing of at least one of implanted and surface electrode for the sensing of information from more than one nerve.
6. The method of claim 1, wherein the nerve is a nerve of a central nervous system.
7. The method of claim 1 wherein the administering is repeated as necessary.
8. The method of claim 1 wherein the controller communicates with an external device.
9. The method of claim 1, wherein the nerve is a mixed motor and sensory nerve.
10. The method of claim 1 wherein the placement is along the nerve at the site of at least one node of Ranvier.
11. A non-transitory computer-readable medium having computer-readable instructions stored thereon, where, upon execution of a processor, the computer-readable instructions cause the processor to:
    calculate a voltage waveform to disrupt creation of action potentials by a nerve based on nerve activity information derived from surrounding at least one nerve with at least one coiled collar, placing at least one sensor for the at least one nerve, at a location along the same nerve, connecting the at least one sensor and the at least one coiled collar to a controller, and obtaining nerve activity information from the at least one sensor and the at least one coiled collar and administer the calculated voltage waveform to the coiled collar to induce a magnetic field.
12. The non-transitory computer-readable medium of claim 11, wherein the voltage waveform consists of one of voltage and voltage regulated current.
13. The non-transitory computer-readable medium of claim 11, wherein the coiled collar performs the non-simultaneous roles of sensor and administering the calculated waveform.
14. The non-transitory computer-readable medium of claim 11 wherein the placing of the at least one sensor comprises the placing of at least one of implanted and surface electrodes.
15. The non-transitory computer-readable medium of claim 11 wherein the placing of the at least one sensor comprises the placing of at least one of implanted and surface electrode for the sensing of information from more than one nerve.
16. The non-transitory computer-readable medium of claim 11, wherein the nerve is a nerve of a central nervous system.
17. The non-transitory computer-readable medium of claim 11 wherein the administering is repeated as necessary.
18. The non-transitory computer-readable medium of claim 11 wherein the controller communicates with an external device.
19. The non-transitory computer-readable medium of claim 11, wherein the nerve is a mixed motor and sensory nerve.
20. The method of claim 11 wherein the placement is along the nerve at the site of at least one node of Ranvier.

* * * * *